United States Patent
Yar et al.

(10) Patent No.: US 10,059,809 B2
(45) Date of Patent: Aug. 28, 2018

(54) MATERIAL AND PREPARATION OF BIOCOMPATIBLE HEMOSTATIC WATER SOLUBLE CHITOSAN

(71) Applicant: COMSATS Institute of Information Technology, Lahore (PK)

(72) Inventors: Muhammad Yar, Lahore (PK); Lubna Shahzadi, Lahore (PK)

(73) Assignee: COMSATS Institute of Information Technology, Lahore (PK)

( * ) Notice: Subject to any disclaimer, the term of this patent is extended or adjusted under 35 U.S.C. 154(b) by 0 days.

(21) Appl. No.: 15/587,064

(22) Filed: May 4, 2017

(65) Prior Publication Data

US 2018/0142067 A1    May 24, 2018

(30) Foreign Application Priority Data

Nov. 18, 2016 (PK) .................................... 727/2016

(51) Int. Cl.
| | |
|---|---|
| *C08G 81/00* | (2006.01) |
| *A01N 43/16* | (2006.01) |
| *A61L 15/42* | (2006.01) |
| *A61L 15/44* | (2006.01) |
| *A61L 15/28* | (2006.01) |
| *A61L 26/00* | (2006.01) |

(52) U.S. Cl.
CPC ............. *C08G 81/00* (2013.01); *A01N 43/16* (2013.01); *A61L 15/28* (2013.01); *A61L 15/425* (2013.01); *A61L 15/44* (2013.01); *A61L 26/0023* (2013.01); *A61L 26/0066* (2013.01); *A61L 2400/06* (2013.01)

(58) Field of Classification Search
CPC . C08G 81/00; A61L 26/0023; A61L 26/0066; A61L 15/44; A61L 15/425; A61L 15/28; A61L 2400/06; A01N 43/16
See application file for complete search history.

(56) References Cited

PUBLICATIONS

Jiang, H.L., et al; Gene Therapy, 2007, vol. 14, p. 1389-1396.*
Bao, X., et al; Biomaterials, 2014, vol. 35, p. 8450-8466.*
Wong, K., et al; Bioconjugate Chemistry, 2006, vol. 17, p. 152-158.*
Casettari, L., et al; Progress in Polymer Science, 2012, vol. 37, p. 659-685.*
Sugimoto, M., et al; Carbohydrate Polymers, 1998, vol. 36, p. 49-59.*
Shahzadi, L., et al; Journal of Biomaterials Applications, 2016, p. 582-593.*
PřichystalováH, et al. "Synthesis, characterization and antibacterial activity of new fluorescent chitosan derivatives", International Journal of Biological Macromolecules 2014;65:234-240.
Hamed I, et al. "Industrial applications of crustacean by-products (chitin, chitosan, and chitooligosaccharides): A review", Trends in Food Science & Technology 2016;48:40-50.
Park GH, et al. "Synthesis, characterization, and biocompatible properties of alanine-grafted chitosan copolymers", Journal of Biomaterials Applications 2016; vol. 30(9):1350-1361.
Yar M, et al. "Triethyl orthoformate mediated a novel crosslinking method for the preparation of hydrogels for tissue engineering applications: characterization and in vitro cytocompatibility analysis", Materials Science and Engineering: C 2015;56:154-164.
Perez M, et al. Chitin and chitosan derivatives. Advances in drug discovery and developments. "Preparation of chitin and chitosan derivatives having mercapto groups Boca Raton", CRC Press Taylor and Francis Group Year 2014: pp. 113-120.

* cited by examiner

*Primary Examiner* — Robert S Jones
(74) *Attorney, Agent, or Firm* — H.C. Park & Associates, PLC (57) ABSTRACT

A water soluble biocompatible hydrogel having an amino sugar linked to a hydrophilic polymer is disclosed. Linkage of the amino sugar and hydrophilic polymer may be provided by an imine-amine bond between an amine of the amino sugar and a primary amine of the hydrophilic polymer. The linkage between the amino sugar and the hydrophilic polymer may be provided by reacting an amine of the amino sugar and a primary amine of the hydrophilic polymer with a formate ester in an acidic solution. Water soluble biocompatible polymer having an amino sugar linked to a hydrophilic polymer may be cast into films, dried into gauze and/or combined with salt solutions to provide injectable gels.

20 Claims, 5 Drawing Sheets

MATERIAL AND PREPARATION OF BIOCOMPATIBLE HEMOSTATIC WATER SOLUBLE CHITOSAN

CROSS-REFERENCE TO RELATED APPLICATION

This application claim priority from and the benefit of Pakistan Provisional Application No. 727/2016, filed Nov. 18, 2016, which is hereby incorporated by reference for all purposes as if fully set forth herein.

BACKGROUND

Field

Water soluble biocompatible polymers including an amino sugar linked to a hydrophilic polymer. Such polymers may be incorporated into gauzes, films, gels and/or sprays.

Discussion of the Background

Amino sugars are saccharides in which a hydroxyl group has been replaced with an amine group. Amino sugars may exists as monosaccharides and/or be incorporated as residues within polymers, such as polysaccharides including sugars, starches and cellulose. One example of a polysaccharide containing an amino sugar is chitosan. Chitosan is a naturally occurring amino sugar polysaccharide consisting of β(1,4) 2-amino-2-deoxy-D-glucopyranose (GlcN) repeating units in addition to a small number of N-acetyl-D-glucosamine (GlcNAc) residues. Amino sugar containing polymers, such as chitosan, have numerous applications due to their excellent biocompatibility, biodegradability, nontoxicity, adsorptive properties, film-forming ability, and antimicrobial activity.

However, the insolubility of chitosan and other amino sugars containing polysaccharides in water and most organic solvents limits their applications in various advanced biomedical fields. Therefore, to impart better biological activity and improve physical properties, like solubility in organic solvents and/or water, special attention has been paid to various derivatives of amino sugars. Derivatives of amino sugars may be prepared by chemically modifying the reactive primary amine and/or hydroxyl groups. Such derivatives may provide new materials with various chemical, physical and biological properties (Přichystalová, H., et al., *International journal of biological macromolecules*, 2014. 65: p. 234). Such amino sugar derivatives may permit polymers providing, for example, improved solubility, controlled drug release, wound healing properties, cell adhesion, antibacterial applications, antioxidant properties, and better carrier efficiency for gene therapy (Perez, M., et al., Boca Raton: CRC Press Taylor and Francis Group, 2014: p. 113).

These amino sugar derivatives may be useful in a variety of diverse industries. For example, amino sugar derivatives may be used in the food industry as antioxidants, food preservatives, antimicrobial packaging and dietary fibers. Amino sugar derivatives may also be utilized in the pharmaceutical, biomedical, textile and cosmetic and dermatological industries (Hamed, I., et al., *Trends in Food Science & Technology*, 2016. 48: p. 40).

The above information disclosed in this Background section is only for enhancement of understanding of the topics discussed below. Consequently, information may be included that has not been previously publicly disclosed.

SUMMARY

A water soluble biocompatible polymer comprising an amino sugar linked to a hydrophilic polymer can provide a structure supporting vasculogensis, angiogenesis, recruitment of endothelia cell progenitors, and/or cell differentiation. Materials incorporating such polymers may be applied to stop bleeding and/or be absorbed by the body. Porous membranes incorporating such polymers may be particularly advantageous.

A water soluble biocompatible polymer comprising an amino sugar linked to a hydrophilic polymer can be synthesized by preparing an acidic solution comprising a polymer having an amino sugar and a hydrophilic polymer. As to facilitate linking the amino sugar to the hydrophilic polymer, a formate ester may be added to the acidic solution. If the hydrophilic polymer has pendant groups containing primary amines, the formate ester may link the hydrophilic polymer to the amino sugar by linking an amine of a pendant group to an amine of the amino sugar. The water soluble biocompatible polymer may be loaded with a drug, such as a hormone.

Linking amines of a pendant group of the hydrophilic polymer and the amino sugar may occur through a two part reaction. First the formate ester may react with either an amine group of the amino sugar or a primary amine of a pendant group on the hydrophilic polymer to form an amide. The newly formed amide may then react with the remaining amine group to form an imine bond between the carbon of the amide and the nitrogen of the remaining amine group. Accordingly, the amino sugar may be linked to a pendant group of a hydrophilic polymer via an imine-amine bond incorporating the primary carbon of the formate ester. The resulting imine-amine bond may provide a water soluble biocompatible polymer having a structure unit according to Formula (I).

Formula (I)

where ASg is an amino sugar, Hp comprises a hydrophilic polymer, R comprises a carbon chain of at least two carbons in length pendant to Hp, and u is a whole number greater than or equal to one.

The formate ester may include triethylorthoformate (TEOF). When added to the acidic solution, TEOF may disassociate to ethyl formate.

The amine containing pendant groups of the hydrophilic polymer are not particularly limited. As to decrease side reactions that might limit, inhibit, compete with or otherwise suppress reactions linking the hydrophilic polymer to the amino sugar, R preferably contains moieties less reactive with formate esters in acidic conditions than primary amines. Accordingly, the primary amine containing pendant groups may comprise ethers, secondary amines and/or ter- tiary amines. Such pendants groups may be provided by diols, glycols, hydroxyalkyl amines, and/or diamines. Another moiety less reactive than primary amines in acidic conditions are saturated carbon chains. Accordingly, the pendant group may contain saturated carbon chains. Saturated carbon chains, may be connected via esters, secondary amines and/or tertiary amines and may be two or more carbons in length. The pendant groups, accordingly, may comprise glycol and/or imine polymers, such as methoxy PEG amine, poly(propylene glycol) bis(2-aminopropyl ether) and/or polyethylene imine. Polymers providing all or a portion of the pendant groups may comprise copolymers. Branched polymers may also comprises all or a portion of the pendant groups. Accordingly, the water soluble biocompatible polymer may comprise a structural unit according to Formula (II)

Formula (II)

where ASg is an amino sugar, Hp comprises a hydrophilic polymer, R comprises a carbon chain of at least two carbons in length, u is a whole number greater than or equal to one, and x is a whole number greater than or equal to zero.

The hydrophilic polymer may comprise a variety of polymers soluble in water, such as glycols, glycol amines, and/or imines. Accordingly, the hydrophilic polymer may comprise methoxy PEG amine, poly(propylene glycol) bis (2-aminpropyl ether) and/or polyethylene imine (PEI). Increased water solubility of the amino sugar, anti-bacterial properties and/or promotion of blood vessel formation may be achieved by including methoxy PEG amine and/or poly (propylene glycol) bis(2-aminopropyl ether) in the hydrophilic polymer. Branched PEI has the advantage of containing several pendant groups containing primary amines. The pendant groups may themselves be branched. Accordingly, the water soluble biocompatible polymer may comprise a structural unit according to Formula (III).

Formula (III)

where ASg is an amino sugar, y is a whole number greater than or equal to one, x is a whole number greater than or equal to zero, and w is a whole number greater than or equal to one.

The amino sugar may include glucosamine, glactosamine. Accordingly, the water soluble biocompatible polymer may comprise a structural unit according to Formula (IV).

Formula (IV)

where Hp comprises a hydrophilic polymer, R comprises a carbon chain of at least two carbons in length pendant to Hp, and u is a whole number greater than or equal to one.

When an amino sugar including glucosamine is linked to a hydrophilic polymer comprising PEI, the hydrophilic biocompatible polymer may have a structural unit represented by Formula (V).

Formula (V)

where y is a whole number greater than or equal to one, x is a whole number greater than or equal to zero, and w is a whole number greater than or equal to one.

The amino sugar may comprise various saccharide residues in which a hydroxyl group has been replaced with an amine group, such as glucosamine and galactosamine. Examples of an amino sugar including glucosamine include, but are not limited to, chitosan. Accordingly, a hydrophilic biocompatible polymer comprising a structural unit according to Formula (V) may be produced by PEI, chitosan and TEOF in an acidic solution. Preferably, the biocompatible polymer comprises 0.4 to 20 weight percent of the hydrophilic polymer.

The water soluble biocompatible polymer may be synthesized by preparing an acidic solution comprising a polymer having an amino sugar, a hydrophilic polymer having pendant groups containing a primary amine and a formate ester. The acidic solution facilitates a linking reaction between the formate ester, an amine of the amino sugar and the amine of a primary amine containing pendant group of the hydrophilic polymer. The linking reaction may be facilitated by dispersing the amino sugar, formate ester and/or hydrophilic polymer within the acidic solution. Ideally, the acidic solution should have a pH of less than 5. The solution may be made acidic with the use of a variety of acids. Mineral acids, such as hydrochloric acid may be used to adjust the pH of the solution to the necessary acidity. Organic acids may also be used to adjust the acidity of the solution. Acetic acid may be preferred from a safety standpoint.

The linking reaction may also be facilitated by heating and/or refluxing the acidic solution. Preferably, the acidic solution is heated to a temperature between approximately 75 and 85° C.

The linking reaction may be allowed to continue for approximately 6 to 24 hours.

Once linked, the polymer solution may be formed into a film. Solvent casting the linked polymer solution may provide a film. A film may also be obtained by spin coating the linked polymer solution onto a suitable surface.

Regardless of whether the polymer is to be formed into film, gelation of the polymer may be desired. Gelation of the linked polymer may be facilitated by freezing the solution, adding salts and/or drying. Salts used to induce gelation preferably are capable of reacting with a protonated amine group of the amino sugar to produce an amine conjugate base. Within the acidic solution, amine groups of the amino sugar may become protonated, giving them a positive charge. The salt may provide a base capable of deprotonating positively charged amine groups. Removing such acidic amine groups, the salt may neutralize the solution as to induce gelation. Accordingly, gelation may facilitated by adding a salt capable of deprotonating acidic amine groups of the amino sugar. The added salt may include sodium hydrogen phosphate, β-glycerophosphate, αβ-glycerophosphate and/or ammonia.

The polymer may be dried to remove water and/or other solvents from the polymer. Drying of the polymer may occur after gelation of the polymer. Exposing the linked polymer to an ambient temperature of approximately 21° C. to 37° C. may be sufficient to induce gelation and/or dry the polymer. Removal of water and/or other solvents from the linked polymer may be facilitated by lyophilizing the linked polymer. A porous gauze may be provided by drying the polymer.

As to facilitate linking the amino sugar to the hydrophilic polymer via the formate ester, it may be preferable to disperse the amino sugar, formate ester and/or hydrophilic polymer within the acidic solution. Accordingly, the acidic solution may be mixed. Mixing of the acidic solution may continue for two hours. As to facilitate dispersion, preferably the acidic solution is mixed in conditions that limit the linking reaction of the formate ester. Accordingly, the acidic solution may be mixed at temperature that does not promote the linking reaction of the formate ester. As such, mixing of the acidic solution may be conducted at room temperature.

As to promote the linking reaction of the formate ester, the acidic solution may be heated. Preferably, the acidic solution is heated to approximately 75-85° C. The linking reaction of the formate ester may also be promoted by refluxing the acidic solution. The acidic solution may be refluxed for approximately two to twenty-four hours; preferably approximately six hours. The acidic solution may be refluxed after being stirred.

As to promote gelation of the water soluble biocompatible polymer, the acidic solution may be reduced in temperature and/or frozen. Preferably, the acidic solution is frozen at a temperature of approximately −20° C. for approximately 12 hours. The polymer may be frozen following being refluxed. Accordingly, the refluxed solution may be frozen at a temperature of approximately −20° C. for approximately 12 hours.

As to promote the removal of water and/or other solvents from the water soluble biocompatible polymer, the polymer may be lyophilized. Preferably, the polymer is lyophilized at approximately −30 to −50° C. for approximately 18 to 48 hours. The polymer may be lyophilized after being frozen. Accordingly, the frozen polymer may be lyophilized at approximately −40° C. for approximately 18 hours. Lyophilizing the polymer may provide a porous gauze.

As to facilitate loading the water soluble biocompatible polymer with a drug, the polymer may be dissolved in a drug solution. The drug loaded onto the polymer is not particularly limited. Examples of suitable drug include hormones, such as thyroxine. Accordingly, dissolving the water soluble biocompatible polymer in a thyroxine solution may provide a thyroxine drug loaded polymer. Once loaded with drug, the polymer may be allowed to gel. Solvent casting the polymer prior to and/or during gelation may provide a film. Gelation of the drug loaded polymer may be facilitated by freezing the solution. After drug loading, the polymer may be dried to remove water and/or other solvents from the polymer. Drying the drug loaded polymer may provide a porous gauze. Removal of water and/or other solvents from the drug loaded polymer may be facilitated by lyophilizing the polymer. Drying of the drug loaded polymer may occur after gelation of the polymer.

The solution of the amino sugar, hydrophilic polymer and formate ester may be made acidic by the addition of various acids. Preferably a sufficient amount of acid is used to lower pH of the solution to less than 5. The necessary acidity may be provided through use of acetic acid at a concentration of approximately 0.5 moles per liter.

The formate ester within the acidic solution is not particularly limited, and may comprise ethyl formate. Ethyl formate may be provided by adding TEOF to the acidic solution. Accordingly, the water soluble biocompatible polymer may be provided utilizing an acidic solution containing 4% TEOF.

The amount of the hydrophilic polymer within the acidic solution is preferably 0.4 to 20 weight percent with respect to the total amount of hydrophilic polymer and amino sugar present in the acidic solution. The hydrophilic polymer is not particular limited, provided it comprises pendant groups having a primary amine. The pendant groups and/or hydrophilic polymer may be branched. Such branching may be provided by using hydrophilic polymer comprising branched polyethyleneimine (PEI). Branched PEI has the advantage of containing several pendant groups containing primary amines. Accordingly, the acidic solution may comprise 0.4 to 20 weight percent of PEI with respect to the total amount of PEI and amino sugar present in the solution acidic solution.

Water soluble biocompatible polymers comprising an amino sugar linked to a hydrophilic polymer may include chitosan and PEI. The chitosan may be linked to PEI by an imine-amine bond between an amine of a glucosamine of chitosan and the primary amine of a pendant group of PEI. The cross-linking carbon of the imine-amine bond may be provided by an ethyl formate provided by TEOF as a new cross-linker. The mass ratio of chitosan and PEI may be 8:2, 9:2, and 9.6:0.4. Such amounts of chitosan and PEI may be soluble in water at room temperature. With regards to the angiogenic potential and the ability to carry hormones, the mass ratio of chitosan to PEI is preferably 9.6:0.4.

The water soluble biocompatible polymer comprising an amino sugar linked to a hydrophilic polymer may be impregnated in a reinforcing material. Such impregnated reinforcing material may have hemostatic and/or antimicrobial properties. When it is desirable that the impregnated reinforcing material swell upon application, or otherwise assist in stopping bleeding, it may be desirable to use polymeric discs and/or cubes. Clothes, such as cotton and silk, may be used as the reinforcing material.

The water soluble biocompatible polymer may be included within an injectable gel. The injectable gel may be provided by adding a salt, such as sodium hydrogen carbonate, to the acid solution of the linked polymer. Preferably, the concentration of the salt is the same as that of the acid in the acidic solution. Gelation of the injectable gel may be induced by the addition of a second salt and/or increase in temperature. The salt added to induce gelation may comprises a salt associated with a base capable of deprotonating positively charged amine groups within the linked polymer. Removing such acidic amine groups, the salt may neutralize the solution as to induce gelation. Accordingly, gelation may be facilitated by adding a salt capable of deprotonating acidic amine groups of the amino sugar. The added salt may include sodium hydrogen phosphate, $\beta$-glycerophosphate, $\alpha\beta$-glycerophosphate and/or ammonia.

The water soluble biocompatible polymer may be included within a spray solution comprising the water soluble biocompatible polymer and a solvent. As the biocompatible polymer is soluble in water, and water is considered safe for medical purposes, water is a preferred solvent. The concentration of the water soluble biocompatible within the spray solution preferably is between approximately 1 to 100 mg/ml. Water soluble biocompatible polymers having inherent blood-clotting capabilities may provide ideal spray solutions.

Water soluble biocompatible polymers comprising an amino sugar linked to a hydrophilic polymer may be included within adhesives, coatings, pharmaceutical preparations, antibacterial dressings textiles, or water treatments.

It is to be understood that both the foregoing general description and the following detailed description are exemplary and not intended to limit the scope of this disclosure. Additional features of the water soluble biocompatible polymers comprising an amino sugar linked to a hydrophilic polymer and materials incorporating such polymers will be apparent if not set forth in the description which follows.

BRIEF DESCRIPTION OF THE DRAWINGS

The accompanying drawings, which are included to provide a further understanding, illustrate embodiments of the water soluble biocompatible polymers comprising a amino sugar linked to a hydrophilic polymer and/or materials incorporating such polymers, and together with the description serve to explain the principles of such polymer and/or materials.

DETAILED DESCRIPTION OF THE ILLUSTRATED EMBODIMENTS

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements.

When an exemplary embodiment may be implemented differently, a specific process order may be performed differently from the described order. For example, two consecutively described processes may be performed substantially at the same time or performed in an order opposite to the described order.

For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

A water soluble biocompatible polymer comprising an amino sugar linked to a hydrophilic polymer can by synthesized by dissolving chitosan in acetic acid solution. To the solution, PEI and triethyl orthoformate may be added. The resulting acidic solution may then be frozen and finally lyophilized until completely dry to obtain a porous scaffold and/or gauze. Solvent casting the solution prior to and/or during gelation may provide a film.

Obtained and observed crosslinking between chitosan and polyethyleneimine that may arise within such an acidic solution is believed to be as given below:

to the amino sugar and the stirring time of the acidic amino sugar solution should be increased until a clear acidic amino sugar solution is achieved. When chitosan is utilized as the amino sugar, 1,000 ml of a 0.5M acetic acidic solution stirred for 24 hours may be necessary to obtain a clear solution comprising 50 g chitosan. After obtaining a clear acidic solution of the amino sugar, the hydrophilic polymer and formate ester may be added. The scaled up solution may then be heated to facilitate the cross-linking reaction. Scaled As can be seen from the above depicted suspected reaction, TEOF decomposes to ethyl formate. The liberated ethyl formate then reacts with a primary amine of a pendant group of PEI and an amine of a glucosamine within chitosan to form an imine-amine bond with the primary carbon of an ethyl formate at its center. It should be noted that while only one pendant group is shown linking PEI to glucosamine, a linkage may be established between the primary amine of any of the depicted pendant groups of PEI.

The linking reaction may be scaled up. When scaling up the reaction, an the amount of acidic solvent initially added up embodiments comprising chitosan, PEI and TEOF may be heated to 80° C. to facilitate the cross-linking reaction.

The acidic solution may be simultaneously stirred, heated and refluxed to facilitate the linking-reaction. Refluxing the solution in the absence of simultaneous stirring may also provide the linking reaction. The linking reaction may also occur with stirring and heating in the absence of refluxing. Heating in the absence of refluxing may be preferable for scaling up the linking reaction in view of ease of production. The absence of refluxing does not appear to affect the linking reaction with regards to scaled up embodiments utilizing an acidic solution comprising chitosan, PEI and TEOF.

As to further illustrate a water soluble biocompatible polymer comprising an amino sugar linked to a hydrophilic polymer, and the production of such a polymer, reference will be made to Examples 1-5. Examples 1-5 were prepared by dissolving chitosan (0.40 g-0.498 g) in acetic acid (0.5M, 10 mL). To the solution, TEOF (4%) and PEI in the amount shown in Table 1 were added. The acidic solutions were then stirred, magnetically, at room temperature for 2 hours followed by refluxing for 2 hours at 80° C.

TABLE 1

|           | Chitosan | PEI   | TEOF |
|-----------|----------|-------|------|
| Example 1 | 0.4      | 0.1   | 4%   |
| Example 2 | 0.45     | 0.05  | 4%   |
| Example 3 | 0.475    | 0.025 | 4%   |
| Example 4 | 0.495    | 0.005 | 4%   |
| Example 5 | 0.498    | 0.002 | 4%   |

NMR (400 MHz, deuterated water) value for Example 5 is 8.30 (broad s), 4.61-4.85 (m), 3.56-3.70 (m), 2.84-2.95 (m), 1.78 (s).

Figure 1:
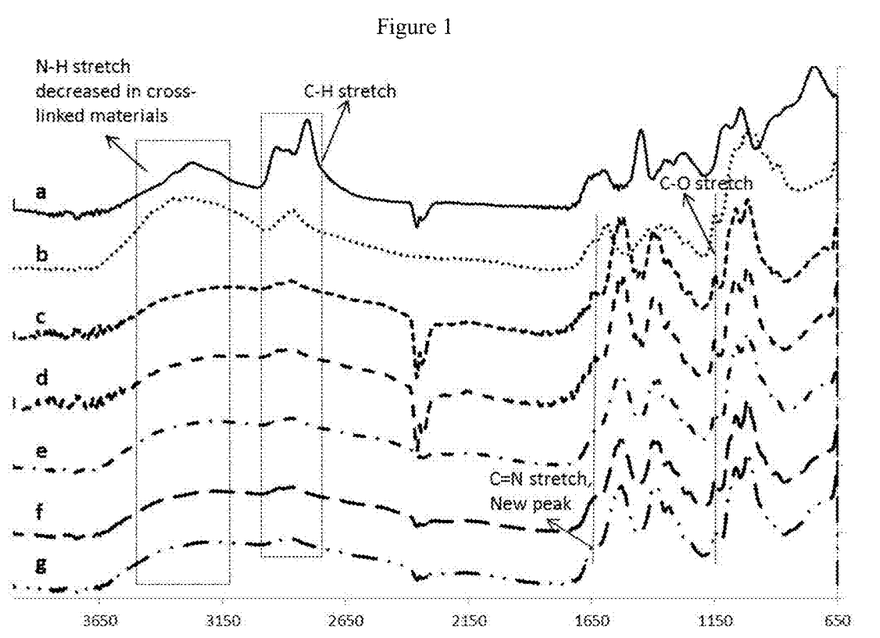
FIG. 1 shows a Fourier Transform Infrared spectrum of chitosan (a), polyethylene imine (b) and five embodiments of water soluble biocompatible polymers comprising amino sugars linked to hydrophilic polymers (c-g).

The chemical structural properties of Examples 1-5 were evaluated by Fourier Transform Infrared (FTIR) Spectroscopy. FTIR spectra were recorded at room temperature using a photo acoustic cell with a carbon background and helium purging, with resolution of 8 $cm^{-1}$, 256 scans over the range of 4000-400 $cm^{-1}$. The FTIR spectrums obtained from Examples 1-5, chitosan and PEI are shown in FIG. 1. Spectrum a of FIG. 1 is that of chitosan. As can be seen from spectrum a, there is a broad peak at 3400-3100 $cm^{-1}$ produced by stretching vibrations of the O—H and N—H moieties of chitosan. Spectrum a also contains a peak at 2838 $cm^{-1}$ attributable to symmetric stretching of alkyl C—H within chitosan. Within the chitosan spectrum, the amide I band or C=O and amide II band or N—H deformation appear at 1658 $cm^{-1}$ and 1572 $cm^{-1}$, respectively. The peaks at 1416 $cm_{-1}$ and 1385 $cm^{-1}$ within chitosan spectrum a are due to $CH_2$ bending. The amide III band within chitosan spectrum appears at 1363 $cm^{-1}$. The peak at 1161 $cm^{-1}$ within chitosan spectrum a can be attributed to C—O stretching frequency. Stretching of saccharide rings within chitosan are observed at 880 $cm^{-1}$ within spectrum a.

Spectrum b of FIG. 1 is that PEI. Within PEI spectrum b, characteristic stretching of N—H provided a peak at 3291 $cm^{-1}$. Peaks at 1579 $cm^{-1}$, 1610 $cm^{-1}$ and 720 $cm^{-1}$ are associated with H—H bending, deforming and rocking vibrations of amines within PEI, respectively. The peaks related to symmetric and asymmetric stretching of C—H bonds within PEI may appear at 2900-2793 $cm^{-1}$ within all spectrums b-g. Peaks associated with the bending of the C_H bonds may appear at 1439 $cm^{-1}$. The peaks in the region of 1350-1000 $cm^{-1}$ of each spectrum a-g may be assigned to —C—N stretching.

Spectrums c-g within FIG. 1 were provided by water soluble biocompatible polymers of Examples 1-5, in reverse order, such that spectrum c was provided by Example 5. Along with the characteristic peaks of chitosan and PEI, spectrums c-g contain new peaks and shifting of existing peaks. Within spectrums c-g, the peak associated with N—H stretching is broadened, which may be the result of inter molecular and intra molecular hydrogen bonding. Also, a clear difference in N—H peak height is present within spectrums c-g, most likely due to the crosslinking of free N—H groups (Yar, M., et al., *Materials Science and Engineering: C*, 2015. 56: p. 154). Crosslinking of PEI and chitosan via the formation of an imine bond is evidenced within spectrums c-g by the peak of —C=N linkage at 1630 $cm^{-1}$. As shown by comparison of spectrums c-g, this peak may became more pronounced and well-defined as the amount of PEI increases. Spectrums c-g also have significant shifting of alkyl and amide bending peaks. This shifting of the alkyl and amide peaks may be attributed to covalent bonding between PEI and chitosan. Accordingly, the shifting of the amide and alkyl peaks within spectrums c-g further evidence the formation of an imine-amine bond linking PEI to chitosan via the primary carbon of ethyl formate derived from TEOF.

The antibacterial properties of Examples 1-5 and chitosan were evaluated by mixing different concentrations (0.1-2.5 mg/ml) from 5 mg/ml stock in water with 0.5 ml Lysogeny Broth (LB) medium. To each broth mixture, 0.01 ml of bacterial culture (*Staphylococcus* sp. or *Escherichia coli*) was added to provide a total adjusted volume of 1 ml. LB broth medium containing only bacterial cultures were included as controls. Eppendorf tubes containing experimental samples and controls were incubated at 37° C. for 48 hours. Following incubation, optical density (OD) of controls and experimental samples were taken at 600 nm using a spectrophotometer. The inhibitory concentration ($IC_{50}$) at which bacterial growth was reduced to half as compare to control based on OD was determined for each of Examples 1-5 and chitosan and is reported in Table 2. The values in parenthesis reported in Table 2 indicate the amount of material in mg/ml at which $IC_{50}$ values were achieved. The values without parenthesis indicate the absorbance values at 600 nm for bacterial cultures.

As shown in Table 2, Example 4 and chitosan were found to be most effective for inhibiting gram negative *Escherichia coli*, with an $IC_{50}$ achieved at 2.0 mg/ml. For *Staphylococcus* sp. (gram-positive), Examples 4 and 5 and chitosan were found to be most effective, with an $IC_{50}$ achieved at 1.8 mg/ml.

TABLE 2

| Material  | *Staphylococcus* sp. (Gram-Positive) | *Escherichia coli* (Gram-Negative) |
|-----------|--------------------------------------|------------------------------------|
| Chitosan  | 0.65(1.8)                            | 0.70(2.0)                          |
| Example 5 | 0.70(1.8)                            | 0.78(2.1)                          |
| Example 4 | 0.70(1.8)                            | 0.70(2.0)                          |
| Example 3 | 0.83(1.9)                            | 0.80(2.5)                          |
| Example 2 | 0.81(1.9)                            | 0.80(2.5)                          |
| Example 1 | 0.84(2)                              | 0.82(2.5)                          |
| Control   | 1.6, 1.7 (mean: 1.65)                | 1.4, 1.7 (mean: 1.55)              |

As Examples 1-5 have anti-bacterial and biocompatible properties, solutions comprising Examples 1-5 may be included in agricultural preparations, such as fertilizers, bactericides, fungicides, and/or pesticides. Similarly, materials prepared from Examples 1-5 may provide clinicians a number of innovative solutions for conventional problems. Materials prepared from Examples 1-5 may include films and/or gauzes.

Figure 2A:
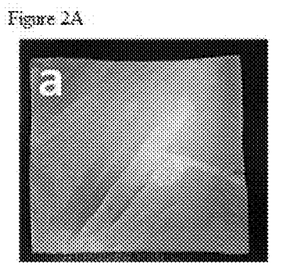
FIG. 2A shows a porous gauze.
Figure 2B:
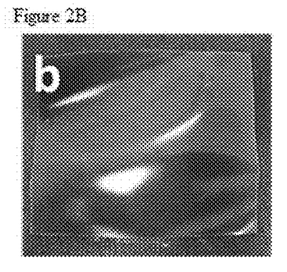
FIG. 2B shows a smooth surface film.
Figure 2C:
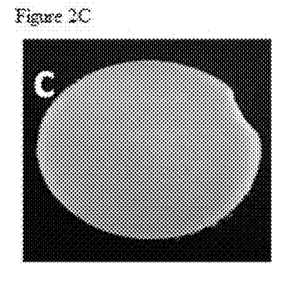
FIG. 2C shows a drug loaded, porous gauze formed from an embodiment of a water soluble biocompatible polymer comprising an amino sugar linked to a hydrophilic polymer.

A film may be obtained from the refluxed solutions of Examples 1-5 by simple solvent casting. FIG. 2B depicts a film obtained from solvent casting Example 5. The film prepared from Example 5 is light weight and comprises a smooth surface.

A porous gauze may be obtained from the refluxed solutions of Examples 1-5 by cooling the solutions, and then freezing the cooled solutions in petri dish at −20° C. for 12 hour. The frozen solutions may then be lyophilized at −40° C. for 18 hours to obtain dry gauzes. FIG. 2A depicts a gauze obtained from Example 5. The gauze prepared from Example 5 is light weight and comprises a porous morphology.

Figure 3A:
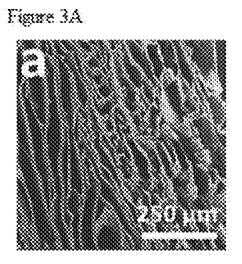
FIGS. 3A, 3B, 3C, 3D, and 3E show SEM images of porous gauzes formed from embodiments of water soluble biocompatible polymers comprising amino sugars linked to hydrophilic polymers.
Figure 3B:
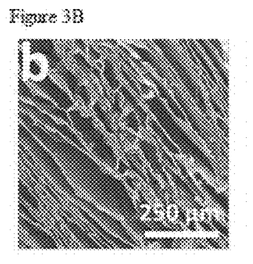
Figure 3C:
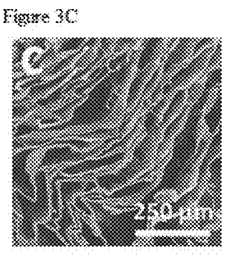
Figure 3D:
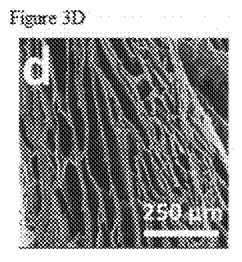
Figure 3E:
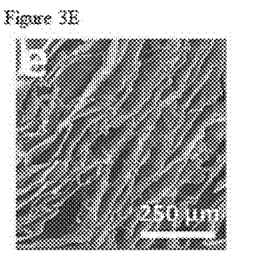

FIG. 3C depicts a drug loaded gauze prepared from the solution of Example 5 by dissolving the obtained water soluble biocompatible polymer in a water solution containing thyroxine at a concentration of 1 mg/ml. The polymer drug mixture was then frozen at −20° C. for 12 hour. The frozen drug loaded solution was then lyophilized at −40° C. for 18 hours to obtain a dry gauze.

The solubility of gauzes prepared from Examples 1-5 was determined in water according to a previously published procedure (Park, G. H., et al., *Journal of biomaterials applications*, 2016. 30(9): p. 1350), with some modifications. A 1×0.5 cm$^2$ piece of gauze was placed in vial and 2 mL of water was added at room temperature. The solutions were then mixed manually with a glass rod and put to rest for 5 minutes before final analysis. A chitosan gauze was used as control. Gauzes prepared from Examples 1-5 were completely soluble in water. Before dissolving, gauzes prepared from Examples 1-5 absorbed water and swelled. Within a minute after being placed in water, gauzes prepared from Examples 1-5 started crumbling into smaller pieces. After 2 minutes the gauzes prepared from Examples 1-5 were 90% dissolved. As gauzes prepared from Examples 1-5 dissolved, a lot of tiny air bubbles were produced in the solution. After ten minutes, the bubbles vanished and a clear solution was obtained. Gauze produced from Example 1, which contained the largest amount of PEI, displayed the greatest solubility in water. All of the gauzes produced from Examples 1-5 completely dissolved within 10 minutes.

The solubility of gauzes prepared from Examples 1-5 in phosphate buffer saline (PBS), ethanol and dimethyl sulfoxide were also examined. While all the gauzes prepared from Examples 1-5 are soluble in in PBS, they are insoluble in ethanol and dimethyl sulfoxide.

For morphological analysis, gauzes prepared from Examples 1-5 were mounted on a stub with conducting carbon tape and analyzed using VEGA 3 TESCAN. The equipment was operated at 15 kV.

Figure 3F:
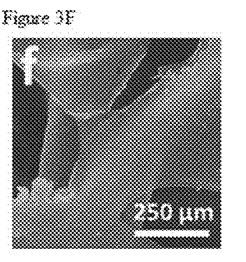
FIG. 3F shows a SEM image of gauze formed from chitosan.

Scanning electron microscope images of porous gauzes prepared from Examples 1-5 are shown in FIGS. 3A-E, respectively. As can be seen from FIGS. 3A-E, all the gauzes exhibited a three-dimensional (3D) porous structure. Such a three dimensional structural may be crucial for the infiltration and proliferation of cells into the gauze when used for wound healing. As shown in FIGS. 3A-E, gauzes prepared from Examples 1-5 comprise a layered, interconnected and irregular open network of pores. Chitosan failed to provide such a network of pores, as evidenced by FIG. 3F. As shown by FIGS. 3A-E, average pore size increases as the amount of chitosan increases. As the concentration of cross-linker ethyl formate was constant in Examples 1-5, the change in pore-size and shape may be mainly due to the increasing ratio of chitosan to PEI. The pure chitosan scaffold, as shown in FIG. 3F, has the largest pores. The average pore-size of gauzes formed from Examples 1-5 and chitosan are provided in Table 3.

TABLE 3

| | Chitosan weight % | Polyethylene Imine weight % | Average Pore Size |
|---|---|---|---|
| Example 1 | 80 | 20 | 42.01 μm ± 25.37 μm |
| Example 2 | 90 | 10 | 50.16 μm ± 28.49 μm |
| Example 3 | 95 | 5 | 55.65 μm ± 31.78 μm |
| Example 4 | 99 | 1 | 60.90 μm ± 29.24 μm |
| Example 5 | 99.6 | 0.4 | 67.50 μm ± 26.36 μm |
| Chitosan | 100 | 0 | 168.68 μm ± 79.69 μm |

The chitosan scaffold was more brittle and displayed pores which were more like cracks in shape.

As with pore size, the amount of amino sugar may also influence the strength of a gauze produced from a water soluble biocompatible polymer comprising an amino sugar linked to a hydrophilic polymer. Gauzes produced from Examples 1-5 became more brittle as the amount of chitosan increased. This decrease in strength may be attributed to the poor mechanical strength of chitosan. Example 1, with highest amount of PEI, is more pliable as compared to Example 5, with least amount of PEI.

The 3D networks may be considered suitable for tissue engineering purposes; indeed, the cell adhesion, proliferation and differentiation functions are assured by 3D morphologies generated. The cell studies revealed that the pore-size of composite gauzes may be suitable for cell growth and proliferation. The 3D structure provided good support and anchorage points to the infiltrating cells.

To investigate the angiogenic potential of gauzes prepared from Example 5, growth of vasculature towards the gauze following implantation into fertilized eggs was assessed. A chitosan gauze was used as a control material.

Fertilized chicken eggs of six days incubation were purchased from Big Bird (Lahore, Pakistan) and incubated till day 8 at 37° C. in a humidified egg incubator (HHD 435). At day 8, a square window (1 cm$^2$) was cut into the shell and removed, and a 1 cm$^2$ gauze prepared from Example 5, 1 cm$^2$ drug loaded gauze prepared from Example 5 loaded with thyroxine, or a 1 cm$^2$ chitosan gauze was placed onto the Chorioallantoic Membrane(CAM). Each egg was implanted with one gauze only. Ten fertilized eggs were used per gauze. An average of 9 eggs survived per batch. The shell window was replaced with parafilm (Bemis Flexible Packaging, USA) and sealed with adhesive tape. After implantation, the eggs were again incubated at 37° C. in a 40% humidified incubator until day 14. At day 14, the gauzes were retrieved and the eggs were sacrificed. Angiogenesis was quantified by taking light microscope pictures just before gauze retrieval and blindly scored by four assessors using images of the retrieved gauzes.

Figure 4A:
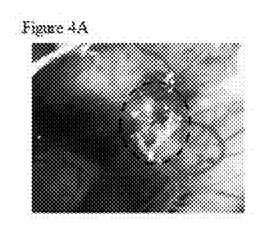
FIG. 4A shows light microscope images of fertilized eggs implanted with a chitosan gauze.
Figure 4B:
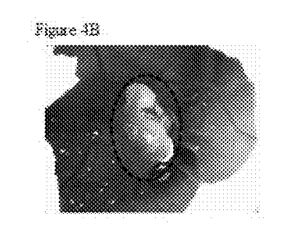
FIG. 4B shows a gauze formed from a water soluble biocompatible comprising an amino sugar linked to a hydrophilic polymer.
Figure 4C:
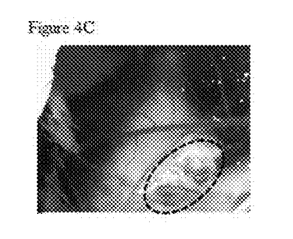
FIG. 4C shows a drug loaded, porous gauze formed from an embodiment of a water soluble biocompatible polymer comprising an amino sugar linked to a hydrophilic polymer.
Figure 5A:
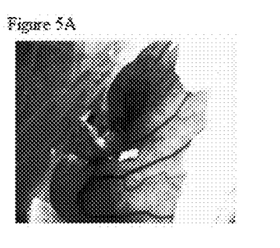
FIG. 5A shows light microscope images of a chitosan gauze.
Figure 5B:
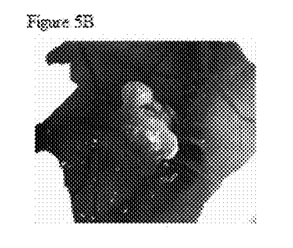
FIG. 5B shows a gauze formed from a water soluble biocompatible comprising an amino sugar linked to a hydrophilic polymer.
Figure 5C:
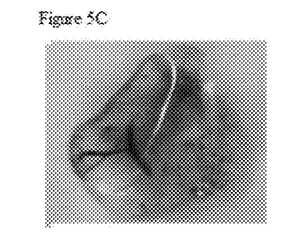
FIG. 5C shows a drug loaded, porous gauze formed from an embodiment of a water soluble biocompatible polymer comprising an amino sugar linked to a hydrophilic polymer after removal from a fertilized egg.

FIG. 4A shows light microscope pictures of at day 14 of fertilized eggs implanted with a chitosan gauze, FIG. 4B shows a gauze prepared from Example 5, and FIG. 4C shows a drug loaded gauze prepared from Example 5. The dotted lines in FIGS. 4A, 4B and 4C encircle the implanted gauzes. As shown by FIGS. 4B and 4C, gauzes prepared from Example 5 exhibited excellent angiogenic behavior. A thick network of vasculature completely surrounds the implanted gauzes. FIG. 5A shows a chitosan gauze, FIG. 5B shows a gauze prepared from Example 5, and FIG. 5C shows a drug loaded gauze prepared from Example 5 removed from fertilized eggs. As shown in FIGS. 4B, 4C, 5B and 5C blood vessels grew into gauzes prepared from Example 5. It should be noted that the gauze shown in FIG. 5C is fixed in paraformaldehyde.

Figure 6A:
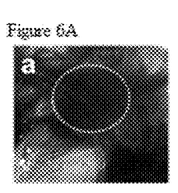
FIGS. 6A, 6B, 6C, and 6D shows a bleeding wound prior to and after placement of a gauze prepared from a water soluble biocompatible polymer comprising an amino sugar linked to a hydrophilic polymer.
Figure 6B:
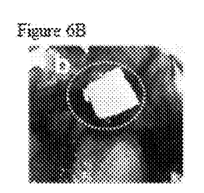
Figure 6C:
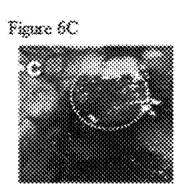
Figure 6D:
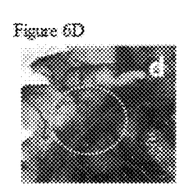

Gauzes prepared from water soluble biocompatible polymers comprising an amino sugar linked to a hydrophilic polymer may also promote clotting. The ability of such gauzes to promote clotting may be determined by placing the gauze on a bleeding wound. FIGS. 6A-D show a bleeding wound prior to and after placement of a gauze prepared from Example 5. FIG. 6A shows the bleeding wound prior to placement of the gauze. FIG. 6B shows the wound immediately following placement of the gauze prepared from Example 5 (i.e. time zero). FIGS. 6C and 6D show the wound 20 and 30 seconds, respectively, after placement of the gauze prepared from Example 5. As shown in FIG. 6C, within 20 seconds of placement of the gauze on the bleeding wound, almost all bleeding was arrested by formation of a clot. Thirty seconds after placement of the gauze, as shown in FIG. 6C, bleeding was completely stopped and the gauze had absorbed the clot.

Figure 7A:
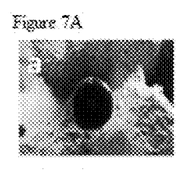
FIGS. 7A, 7B, 7C, and 7D shows avian blood prior to and after placement of a gauze prepared from a water soluble biocompatible polymer comprising an amino sugar linked to a hydrophilic polymer.
Figure 7B:
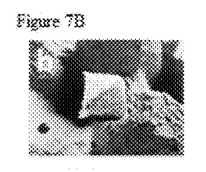
Figure 7C:
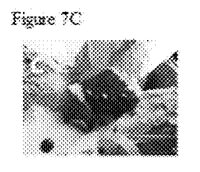
Figure 7D:
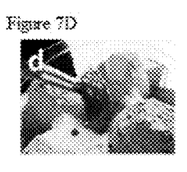

The ability of gauzes prepared from water soluble biocompatible polymers comprising an amino sugar linked to a hydrophilic polymer to promote clotting may also be determined by placing the gauze on blood. FIGS. 7A-D show a gauze prepared from Example 5 placed on avian blood. FIG. 7A shows the avian blood sample prior to placement of the gauze. FIG. 7B shows the blood sample immediately following placement of the gauze. FIG. 7C and FIG. 7D show the blood sample 20 and 30 seconds, respectively, after placement of the gauze prepared from Example 5. As shown in FIG. 7C, within 20 seconds the gauze prepared from Example 5 had induced complete clotting of the blood sample. Thirty seconds after placement, as shown in FIG. 8C, the clot was absorbed by the gauze.

A gauze may comprise a reinforcing material impregnated with a water soluble biocompatible polymer comprising an amino sugar linked to a hydrophilic polymer. The reinforcing material may comprise a fabric, such as cotton and/or silk. Polymeric discs and/or cubes may also be included within the reinforcing material. Impregnating the reinforcing material with the biocompatible polymer may be accomplished by soaking the reinforcing material in a solution of the biocompatible polymer. As an example, a cotton bandage may be soaked in an aqueous solution of Example 5. After soaking for an hour, the cotton bandage may be removed from the Example 5 solution and allowed to dry, as to provide a hemostatic bandage.

In addition to films and gauzes, the water soluble biocompatible polymer may be included within injectable gels. An injectable gel including the water soluble biocompatible polymer may be liquid at room temperature. Gelation may be induced by raising the temperature of the injectable to get to physiological temperatures. Gelation of the injectable gel may be triggered by the addition of a salt capable of deprotonating acidic amine groups of the amino sugar. The added salt may include sodium hydrogen phosphate, β-glycerophosphate, αβ-glycerophosphate and/or ammonia.

An injectable liquid gel comprising a water soluble biocompatible polymer comprising an amino sugar linked to a hydrophilic polymer may be provided by adding a salt to an acidic solution comprising the biocompatible polymer. Preferably the salt concentration is approximately that of the acid in the acid solution. Gelation of the biocompatible polymer within the injectable gel may be facilitated by adding a second salt to the solution and/or increasing the temperature of the polymer-salt solution to a physiological temperature. By way of example, sodium hydrogen carbonate as a first salt was added to Example 5. The resulting salt mixture remained liquid at room temperature. Following addition of sodium hydrogen phosphate as a second salt and elevation to a physiological temperature of. 37° C., the Example 5 salt mixture gelled. The pH of the gel is within a physiological range, making it ideal for various medical applications.

A spray solution containing a solvent and a water soluble biocompatible polymer comprising an amino sugar linked to a hydrophilic polymer may be provided by dissolving the water soluble biocompatible polymer in an appropriate solvent. As the water soluble biocompatible polymer is soluble in water, and water is considered safe for medical application, water may be a preferred solvent. The concentration of the water soluble biocompatible within the spray solution preferably is between approximately 1 to 100 mg/ml.

Further embodiments of water soluble biocompatible polymers comprising an amino sugar linked to a hydrophilic polymer may include adhesives, coatings, pharmaceutical preparations, antibacterial dressings textiles, or water treatments.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. A water soluble biocompatible polymer compound comprising a structural unit according to Formula (I)

wherein ASg is an amino sugar,
wherein Hp comprises hydrophilic polymer,
wherein R comprises a carbon chain of at least two carbon in length, R pendant to Hp, and
wherein u is a whole number greater than or equal to one.

2. The polymer according to claim 1, wherein Hp comprises polyethylene imine.

3. The polymer according to claim 1, having between approximately 0.4 wt % to 20 wt % Hp with respect to the total amount of ASg and Hp.

4. The polymer according to claim 1, further comprising a salt solution.

5. The polymer according to claim 4, wherein the salt solution comprises sodium hydrogen carbonate.

6. A method for the manufacturing a biocompatible polymer compound, comprising:
providing an acidic solution comprising:
a polymer comprising an amino sugar;
a hydrophilic polymer comprising a pendant group having a primary amine; and
a formate ester;
stirring the solution at room temperature; and
heating the stirred solution.

7. The method of claim 6, further comprising refluxing the stirred solution.

8. The method of claim 7, wherein refluxing the stirred solution is conducted at approximately 75 to 85° C. for approximately two to twenty-four hours.

9. The method of claim 6, wherein the acidic solution has a pH of less than 5.

10. The method of claim 6, wherein the formate ester of the acidic solution comprises triethyl orthoformate, and wherein the concentration of the formate ester in the acidic solution is approximately 4%.

11. The method of claim 6, wherein the hydrophilic polymer of the acidic solution comprises polyethylene imine, and wherein the concentration of the hydrophilic polymer in the acidic solution is approximately 0.4 wt % to 20 wt % with respect to a total amount of the hydrophilic polymer and the polymer comprising an amino sugar.

12. The method of claim 6, wherein the polymer comprises an amino sugar containing chitosan.

13. The method of claim 6, wherein stirring the acidic solution is continued for approximately two hours.

14. The method of claim 6, further comprising freezing the stirred solution.

15. The method of claim 14, wherein freezing the stirred solution is conducted at approximately −20° C. for approximately twelve hours.

16. The method of claim 6, further comprising lyophilizing the stirred solution.

17. The method of claim 16, wherein lyophilizing the stirred solution is conducted at approximately −30 to −50° C. for approximately eighteen to twenty-four hours.

18. The method of claim 6, further comprising solvent casting the stirred solution.

19. A water soluble biocompatible polymer compound comprising a structural unit according to Formula (V)

wherein y is a whole number greater than or equal to one,
wherein x is a whole number greater than or equal to zero, and
wherein w is a whole number greater than or equal to one.

20. The polymer according to claim 19, comprising between approximately 0.4 wt % to 20 wt % polyethylene imine.

* * * * *